(12) United States Patent
Coenen

(10) Patent No.: US 8,356,510 B2
(45) Date of Patent: Jan. 22, 2013

(54) FORMATION CORE SAMPLE HOLDER ASSEMBLY AND TESTING METHOD

(75) Inventor: Joseph Guillaume Christoffel Coenen, Rijswijk (NL)

(73) Assignee: Shell Oil Company, Houston, TX (US)

( * ) Notice: Subject to any disclaimer, the term of this patent is extended or adjusted under 35 U.S.C. 154(b) by 509 days.

(21) Appl. No.: 12/597,202

(22) PCT Filed: Apr. 24, 2008

(86) PCT No.: PCT/EP2008/055003
§ 371 (c)(1),
(2), (4) Date: Oct. 23, 2009

(87) PCT Pub. No.: WO2008/132132
PCT Pub. Date: Nov. 6, 2008

(65) Prior Publication Data
US 2010/0126266 A1    May 27, 2010

(30) Foreign Application Priority Data

Apr. 26, 2007 (EP) .................................. 07107024

(51) Int. Cl.
*G01N 15/08* (2006.01)
(52) U.S. Cl. ............................................. 73/38
(58) Field of Classification Search ................ 378/208
See application file for complete search history.

(56) References Cited

U.S. PATENT DOCUMENTS

| | | | |
|---|---|---|---|
| 2,345,935 A | | 4/1944 | Hassler .............................. 73/51 |
| 4,379,407 A | * | 4/1983 | Masse et al. ..................... 73/579 |
| 4,419,314 A | * | 12/1983 | Bush ............................. 264/130 |
| 4,563,726 A | | 1/1986 | Newcomb et al. ............. 362/34 |
| 4,669,299 A | | 6/1987 | Closmann .......................... 73/38 |
| 4,688,238 A | * | 8/1987 | Sprunt et al. ...................... 378/4 |
| 4,710,948 A | * | 12/1987 | Withjack ....................... 378/208 |
| 5,065,421 A | | 11/1991 | Morineau et al. ............. 378/208 |
| 5,297,420 A | * | 3/1994 | Gilliland et al. .................. 73/38 |
| 5,363,692 A | | 11/1994 | Lafargue et al. .................. 73/38 |
| 5,493,226 A | | 2/1996 | Honarpour et al. ........... 324/376 |
| 5,698,772 A | | 12/1997 | Deruyter et al. .................. 73/38 |

FOREIGN PATENT DOCUMENTS

| | | | |
|---|---|---|---|
| GB | 2185114 A | * | 7/1987 |
| GB | 1257835 | | 12/1991 |

* cited by examiner

*Primary Examiner* — Peter Macchiarolo
*Assistant Examiner* — Tamiko Bellamy

(57) ABSTRACT

A core sample holder assembly for performing laboratory core flooding experiments with a core sample:

a pressure chamber provided by a tubular hull made of a carbon fiber composite material and an aluminum liner, and a pair of disk-shaped flanges;

a flexible core sample holder sleeve within the pressure chamber, which sleeve comprises a tubular steel sheet with a plastic inner lining;

an opening for injecting oil into an annular space between the hull and the sleeve;

pressure control means for maintaining the oil at a predetermined pressure;

an fluid injection port for injecting a fluid into a cylindrical core sample within the sleeve;

a fluid outlet port arranged in the other flange for discharge of fluid from the core sample; and means for monitoring the migration of injected and/or pore fluid through the pores of the core sample.

10 Claims, 1 Drawing Sheet

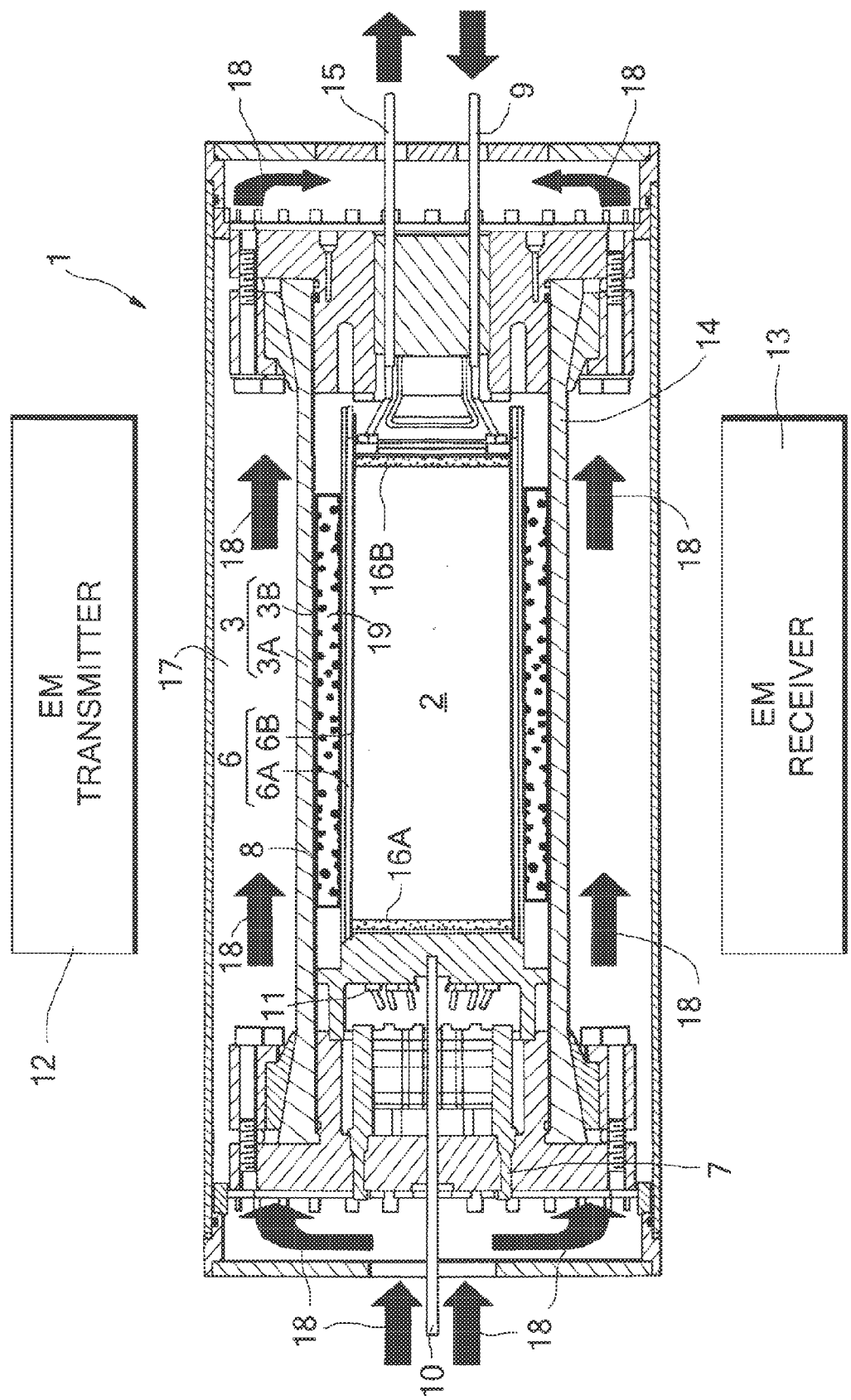

FORMATION CORE SAMPLE HOLDER ASSEMBLY AND TESTING METHOD

PRIORITY CLAIM

The present application claims priority of PCT Application EP2008/055003, filed 24 Apr. 2008, which claims priority to European Patent Application No. 07107024.7 filed 26 Apr. 2007.

BACKGROUND OF THE INVENTION

The invention relates to a formation core sample holder assembly and a core testing method. In the oil and gas production industry it is common practice to take, when an exploration or production well is being drilled, one or more cylindrical core samples of hydrocarbon containing or other formation and to subsequently perform one or more tests with this core sample in a laboratory.

During these tests the sample is arranged in a pressurized sample holder assembly, in which the temperature and pressure are substantially similar to the ambient pressure and temperature within the hydrocarbon containing or other formation from which the sample has been taken, and a treating, completion and/or stimulation fluid is injected into the sample to determine an optimum composition of the treating, completion and/or stimulation fluid and/or an optimum injection regime.

A known core holder assembly in which the core sample is contained within an elastomeric sleeve is known as the Hassler core holder and is described in U.S. Pat. No. 2,345,935 issued to G. L. Hassler. Other core holder assemblies equipped with elastomeric sleeves are known from U.S. Pat. No. 4,563,726 issued to Core Laboratories Inc. and from U.S. Pat. No. 5,698,772 issued to Institut Francais du Petrole.

A problem of the known core sample holder assemblies is that they are not suitable to maintain the core sample at elevated temperature and pressure while electromagnetic radiation is transmitted through the core sample to monitor the fluid migration within the core sample.

A further problem of the known core sample holder assemblies is that they are provided with elastomeric sleeves which are not suitable for use at high temperatures of more than 300 degrees Celsius and/or are susceptible to fatigue, thermal break down and/or material degradation.

A further problem of the known core holder assemblies is that they are provided with elastomeric sleeves, which are not suitable to exposure to certain chemicals, such as hydrogen sulphide and carbon dioxide.

It is an object of the present invention to provide a core holder assembly and core testing method, which provide a solution to these problems.

SUMMARY OF THE INVENTION

In accordance with the invention there is provided a core sample holder assembly for performing laboratory core flooding experiments with a core sample taken from a hydrocarbon containing formation, comprising:

a pressure chamber provided by a tubular hull, which comprises a carbon fiber composite material and an aluminum liner, and a pair of disk-shaped flanges arranged at opposite sides of the tubular hull;

a flexible core sample holder sleeve, which is arranged within the pressure chamber, is sealingly secured to the disk-shaped flanges and comprises a tubular steel sheet with a plastic lining;

an opening for injecting oil through one of the disk-shaped flanges into an annular space between the tubular hull and the flexible sleeve;

pressure control means for maintaining the oil in the annular space at a predetermined pressure;

an fluid injection port for injecting a fluid through one of the disk-shaped flanges into pores of a cylindrical core sample which is in use arranged within the flexible sleeve;

a fluid outlet port arranged in the other disk-shaped flange for discharge of pore and/or injected fluid from the pores of the core sample; and means for monitoring the migration of injected and/or pore fluid through the pores of the core sample by transmitting electromagnetic radiation through the core via the surrounding hull, oil and flexible sleeve.

The plastic inner lining preferably comprises an industrial plastic selected from the group of polytetrafluoroethylene (PTFE), Polyetheretherketone (PEEK), Celazole Polybenzimidazole (celazole BPI), Polyamide 46 (Stanyl PA46) and Kapton polymide. Optionally, the tubular steel sheet is less than 0.2 mm thick and is made of a Hasteloy-C steel grade. The tubular steel sheet may be wrapped in a thermally insulating blanket made of a porous ceramic material, which blanket fills at least a substantial portion of the annular space.

In accordance with the invention there is further provided a method for performing laboratory core flooding experiments with a core sample taken from a hydrocarbon containing formation, which method comprises:

a) inserting the core sample into a core sample holder assembly comprising:
   a pair of disk-shaped flanges arranged at opposite sides of a tubular hull, which comprises a carbon fiber composite material and an aluminum liner;
   a flexible sleeve, which is arranged within the pressure chamber and is sealingly secured to the disk-shaped flanges and comprises a tubular steel sheet with a plastic inner lining;
   an opening for injecting oil through one of the disk-shaped flanges into an annular space between the tubular hull and the flexible sleeve;
   pressure control means for maintaining the oil in the annular space at a predetermined pressure;
   an fluid injection port for injecting a fluid through one of the disk-shaped flanges into pores of the core sample which is arranged within the flexible sleeve;
   a fluid outlet port arranged in the other disk-shaped flange for discharge of pore and/or injected fluid from the core sample; and
b) monitoring the migration of injected and/or pore fluid through the pores of the core sample by transmitting electromagnetic radiation through the core via the surrounding hull, oil and flexible sleeve.

The electromagnetic radiation may be transmitted by an X-ray source and/or a Computer Tomography (CT) scanning device.

These and other features, embodiments and advantages of the core holder assembly and core testing method according to the invention are described in the accompanying claims, abstract and the following detailed description of a preferred embodiment in which reference is made to the accompanying drawing.

BRIEF DESCRIPTION OF THE DRAWINGS

FIG. 1 is a schematic longitudinal sectional view of a core holder assembly according to the invention.

DETAILED DESCRIPTION OF THE DEPICTED EMBODIMENT

FIG. 1 depicts a core holder assembly 1 according to the invention in which a cylindrical core sample 2 taken from a hydrocarbon containing formation is tested.

The core holder assembly 1 comprises:

a pressure chamber provided by a tubular hull 3, which comprises an outer layer 3A made of a carbon fiber composite material and an inner aluminum liner 3B, and a pair of disk-shaped flanges 4,5 that are arranged at opposite sides of the tubular hull 3;

a flexible core holder sleeve 6, which is arranged within the tubular hull and is sealingly secured to the disk-shaped flanges and comprises a tubular steel sheet 6A with an inner lining 6B comprising polytetrafluoroethylene (PTFE), which is also known as Teflon (Teflon is a trademark);

an opening 7 for injecting oil through one of the disk-shaped flanges 5 into an annular space 8 between the tubular hull 3 and the flexible sleeve 6;

pressure control means for maintaining the oil in the annular space 8 at a predetermined pressure;

an fluid injection port 9 for injecting a fluid through one of the disk-shaped flanges 4 into a cylindrical core sample 2 which is arranged within the flexible sleeve 6;

a fluid outlet port 10 arranged in the other disk-shaped flange 5 for discharge of pore and/or injected fluid from the core sample 2; and means 11 for monitoring the migration of injected and/or pore fluid through the pores of the core sample by transmitting electromagnetic radiation through the core via the surrounding hull, oil and flexible sleeve.

Instead of PTFE the plastic inner lining may comprise another high grade industrial plastic selected from the group of Polyetheretherketone (PEEK), Celazole Polybenzimidazole (celazole BPI), Polyamide 46 (Stanyl PA46) and Kapton polymide.

The tubular steel sheet 6A is less than 0.2 mm, preferably about 0.1 mm, thick and is made of a Hasteloy-C steel grade. The tubular steel sheet 6A is wrapped in a thermally insulating blanket 19, which is made of a porous ceramic material and fills at least a substantial portion of the annular space 8.

The oil in the annular space 8 has a boiling temperature between 300 and 340 degrees Celsius at 1 bar.

The core holder assembly 1 is provided with one or more thermocouples 11 that are pierced into a tail end of the tested core, which is located adjacent to said other disk-shaped flange.

An Electro Magnetic (EM) transmitter 12, such as an X-Ray source and/or a Computer Tomography (CT) scanning source is arranged above the core sample holding device 1 and a Electro Magnetic (EM) receiver 13, such as an X-Ray and/or CT scanning monitor, is arranged below the core sample holding device 1.

The core holder assembly 1 according to the invention allows fluid flow experimenting under realistic high-pressure, high temperature (HPHT) field conditions while using X-ray scanning and/or Computerized Tomography (CT) scanning with the EM transmitter and receivers 12 and 13.

The core holder assembly 1 may be used for core flooding experiments for the experimental study of process parameters playing a role during steam injection processes for thermal Enhanced Oil Recovery (EOR) of HeaVy Oil (HVO) fields. The objective is to shed light in the fundamentals of heat transfer and oil mobilization prevailing during steam flooding and cyclic steam stimulation.

The core holder assembly 1 may provide a steam injection core flooding system for experimenting at realistic field pressure levels up to 125 bar and steam temperatures up to 325° C.

The core holder assembly 1 replaces a conventional Hassler type core holder in which the core 2 is confined by a flexible sleeve, pressurized by hydraulic oil. For delivering the over burden pressure to the sleeve 6 hydraulic oil is used.

The combination of High Pressure, High Temperature (HPHT) core flooding experiments and Computerized Tomography scanning impose a special challenge to the material used in the core holder assembly 1. HPHT experiments in combination with X-ray transparency for CT-scanning form a paradigm in material science and requires innovation on the applied materials.

FIG. 1 shows the following key features of the core holder assembly 1 according to the invention:

A) The tubular hull 3 comprises a layer 3A of a carbon fiber-epoxy composite material. This composite material is three to four times stronger than steel and at the same time offers very low heat conduction as well as low absorption for X-rays. The core holder 1 according to the invention is configured to accommodate a core of a four inch 4" (about 10 cm) diameter and 1 foot (about 30 cm) length for 100 bar static pressure and 50° C. At the inner wall of the carbon fiber composite layer 3A is an Aluminum barrel 3B of 1 mm thickness to provide hydraulic sealing for the sleeve oil.

Usually in conventional Hassler core holders known from U.S. Pat. No. 2,345,935, sealing of the core 2 is provided by a flexible elastomer sleeve. The high temperatures prevailing under modern R&D experiments (e.g. steam injection experiments at a temperature of about 320° C.) put a strong challenge to these materials in terms of fatigue, thermal break down or material degradation. For instance a well-know material such as Viton falls short for our steam testing conditions.

B) The flexible sleeve 6 comprises a thin sheet of Hasteloy-C steel foil 6A and a Teflon back-up layer 6B. The advantages of this thin steel foil 6A are that it is strong up and beyond 1000° C., it is resistant against puncturing by sand grains and it forms an outer layer providing an absolute hermetically sealed barrier to the super hot steam as well as to solution gas and toxic oil components eventually escaping from the core. A soft Teflon cylinder 6B is used as a second, semi flexible layer to seal the core and prohibit bypassing of fluids along the core sample 2. The whole forms a wear, heat and chemical resistant flexible sleeve arrangement. Experiments indicate that thin 0.1 mm thick metal foil 6A, when being wrapped around a core 2, does not create CT-image distorsion or artefacts. An advantage of the Steel-Teflon combination 6A,6B is that it allows sleeve compression as well as expansion. These properties are important during thermal recovery experiments as well as contaminated gas experiments.

C) For delivering the over burden pressure in the annular space 8 surrounding the sleeve 6 and core sample 2 hydraulic oil is used. In order to create a core holder with hot inner parts and a relative cold outer hull, Shell Thermia-B (Shell and Thermia-B are trademarks) oil is used with a boiling point temperature of 320° C. at 1 bar, a low thermal conductivity and exhibiting no thermal degradation.

D) Reduction of the heat transport from the hot core to the sleeve is achieved by reducing heat convection of the hydraulic oil in the annular space 8 of the core holder 1 by wrapping the core 2 and sleeve 6 with a porous ceramic blanket. This blanket keeps the hydraulic oil substantially stagnant within the annular space 8. The heat transport from the hot core 2 to the outer tubular hull 3 comprising a carbon fiber composite material 3A is substantially limited to heat conduction through the sleeve 6 and the static Thermia-B oil in the annular space 8.

E) The design of the steam injector assembly 14 in the disk shaped flange 4 at the front of the core holder assembly 1.

The steam injector assembly 14 is a robust metal part in case fluid flow experiments are carried out using high pressure steam injection. The steam injector assembly is provided with a fluid injection port 9 giving passage for pressurized hot steam from a high-pressure tubing to the core 2. In cyclic steam stimulation it also allows the produced steam, condense water and oil to flow in backward direction via a second steel tubing 15 passing through the first disk-shaped flange 4 adjacent to the steam injector assembly 14. In order to reduce heat loss in lateral direction the mass of the injector assembly is reduced by designing it into a hollow dome shape. The injector assembly 14 also offers sufficient rigidity to the pressure load (100 bar). The steam injector assembly 14 is thermally insulated from the metal end flange by a flat ring of "Isoplan" fiber mat with low thermal conductivity.

F) Temperature and pressure sensors 11 are mounted inside the core holder assembly 1 to provide real-time data on the thermodynamic conditions during the progress of the fluid flow experiments. Because sensor taps are difficult to construct on the thin sleeve 6 it is desired to have full CT-coverage of the 1-foot (about 30 cm) long core, no sensor taps were used in the sleeve 6. Therefore the pressure and/or temperature sensors 11 are guided via the disk shaped flange 5 at the tail part of the core holder assembly 1, right under the PTFE inner lining 6B of the sleeve 6 and at the rim of the core 2 in upstream direction.

G) Elongate thermocouples with very small diameter (0.8 mm) are used as temperature sensors 11. In an experiment eleven temperature sensors provided by elongate thermocouples were inserted at different positions in the core sample 2. One extra long thermocouple was inserted all the way from the tail end upstream to the front face of the core close to the steam injector assembly 14 to guard the steam temperature upon injection in the core 2.

In the experiment eleven pressure sensors are also guided through the core sample 2 to monitor the pressure in the core sample 2. The pressure sensors each comprise a membrane which is connected via a, hydraulic oil filled, thin and long steel capillary tube to a pressure gauge mounted outside the core holder assembly 1. Micro Electro Mechanical System (MEMS) miniature pressure transducers with piezo resistive sensors were used as pressure gauges. These sensors offer minimal fluid displacement under pressure and minimize the risk on clogging of the capillary entrance e.g. by bitumen.

The core sample holder assembly according to the invention is furthermore provided with sandscreen assemblies 16A and 16B at the front and tail ends of the core sample 2 and with an air cooling system 17 via which cool air is pumped through a cooling chamber surrounding the tubular hull 3 and the disk-shaped flanges 4 and 5.

The core holder assembly 1 according to the invention provided with a flexible steel sheet 6A may be used in conducting fluid flow experiments under harsh conditions (very high pressure and temperatures) using super hot steam, hot water and/or contaminated gasses such as $H_2S$, $CO_2$, chemical injectants and/or chemically aggressive stimulation and/or treating fluids.

What is claimed is:

1. A core sample holder assembly for performing laboratory core flooding experiments with a core sample taken from a hydrocarbon containing formation, comprising:

a pressure chamber provided by a tubular hull, the hull comprising a carbon fiber composite material and an aluminum liner, and a pair of disk-shaped flanges arranged at opposite sides of the tubular hull;

a flexible core sample holder sleeve comprising a tubular steel sheet with a plastic inner lining, the sleeve being arranged within the pressure chamber and sealingly secured to the disk-shaped flanges wherein the tubular steel sheet is wrapped in a porous thermally insulating blanket;

an opening for injecting oil through one of the disk-shaped flanges into an annular space between the tubular hull and the flexible sleeve;

pressure control means for maintaining the oil in the annular space at a predetermined pressure;

an fluid injection port for injecting a fluid through one of the disk-shaped flanges into pores of the core sample, which is in use arranged within the flexible sleeve;

a fluid outlet port arranged in the other disk-shaped flange for discharge of pore and/or injected fluid from the pores of the core sample; and means for monitoring the migration of injected and/or pore fluid through the pores of the core sample by transmitting electromagnetic radiation through the core via the surrounding hull, oil and flexible sleeve.

2. The core sample holder assembly of claim 1, wherein the tubular steel sheet is less than 0.2 mm thick.

3. The core sample holder assembly of claim 1, wherein the tubular steel sheet is made of a Hasteloy-C steel grade or a normal steel grade with a corrosion inhibiting coating.

4. The core sample holder assembly of claim 1, wherein the plastic inner lining comprises an industrial plastic selected from the group of polytetrafluoroethylene(PTFE), Polyetheretherketone (PEEK), Celazole Polybenzimidazole (celazole BPI), Polyamide 46 (Stanyl PA46) and Kapton polymide.

5. The core sample holder assembly of claim 1 wherein the thermally insulating blanket is made of a ceramic material and fills at least a substantial portion of the annular space.

6. The core sample holder assembly of claim 1, wherein the oil has a boiling temperature between 300 and 340 degrees Celsius at 1 bar.

7. The core sample holder assembly of claim 1, wherein the core holder assembly is provided with one or more thermocouples that are pierced into a tail end of the tested core, which is located adjacent to said other disk-shaped flange.

8. The core sample holder assembly of claim 1, wherein the electromagnetic radiation is transmitted by an X-ray source and/or a Computer Tomography (CT) scanning device.

9. A method for performing laboratory core flooding experiments with a core sample taken from a hydrocarbon containing formation, the method comprising:

a) inserting the core sample into a core sample holder assembly comprising:

a pair of disk-shaped flanges arranged at opposite sides of a tubular hull, said hull comprising a carbon fiber composite material and an aluminum liner;

a flexible sleeve, which is arranged within the pressure chamber and is sealingly secured to the disk-shaped flanges and comprises a tubular steel sheet with a plastic inner lining wherein the tubular steel sheet is wrapped in a porous thermally insulating blanket;

an opening for injecting oil through one of the disk-shaped flanges into an annular space between the tubular hull and the flexible sleeve;

pressure control means for maintaining the oil in the annular space at a predetermined pressure;

an fluid injection port for injecting a fluid through one of the disk-shaped flanges into pores of the core sample which is arranged within the flexible sleeve;

a fluid outlet port arranged in the other disk-shaped flange for discharge of pore and/or injected fluid from the core sample; and b) monitoring the migration of injected and/or pore fluid through the pores of the core sample by transmitting electromagnetic radiation through the core via the surrounding hull, oil and flexible sleeve.

10. The method of claim 9, wherein the electromagnetic radiation is transmitted by an X-ray source and/or a Computer Tomography (CT) scanning device.

* * * * *